US007807118B2

(12) United States Patent
Green et al.

(10) Patent No.: US 7,807,118 B2
(45) Date of Patent: Oct. 5, 2010

(54) DECONTAMINATION SYSTEM (75) Inventors: Bruce Philip Green, Northampton (GB); Paul Swinney, Newmarket (GB)

(73) Assignee: Tristel PLC, Cambridgeshire (GB)

( * ) Notice: Subject to any disclaimer, the term of this patent is extended or adjusted under 35 U.S.C. 154(b) by 491 days.

(21) Appl. No.: 10/935,030

(22) Filed: Sep. 7, 2004

(65) Prior Publication Data
US 2006/0051266 A1    Mar. 9, 2006

(51) Int. Cl.
*A61L 2/00* (2006.01)
*A61L 9/00* (2006.01)
*A61L 2/18* (2006.01)

(52) U.S. Cl. .................... 422/292; 422/28; 422/29; 422/37

(58) Field of Classification Search ............. 422/292; 604/385.06; 224/932; 206/812; D9/734
See application file for complete search history.

(56) References Cited

U.S. PATENT DOCUMENTS

| 2,833,624 | A |   | 5/1958  | Sprauer |
| 3,568,627 | A | * | 3/1971  | Selinger et al. ............. 116/207 |
| 3,933,274 | A |   | 1/1976  | Emmons et al. |
| 4,013,761 | A |   | 3/1977  | Ward et al. |
| 4,330,531 | A | * | 5/1982  | Alliger ........................ 424/661 |
| 4,345,716 | A |   | 8/1982  | Armstrong et al. |
| 4,361,235 | A |   | 11/1982 | Gautier |
| 4,438,871 | A |   | 3/1984  | Eckert |
| RE31,779  | E |   | 12/1984 | Alliger |
| 4,516,726 | A |   | 5/1985  | Hoie |
| 4,534,952 | A |   | 8/1985  | Rapson et al. |
| 4,538,919 | A |   | 9/1985  | Bohnensieker |
| 4,646,973 | A |   | 3/1987  | Focaracci |

(Continued)

FOREIGN PATENT DOCUMENTS

DE    37 14 699    1/1988

(Continued)

OTHER PUBLICATIONS

Rostker, Bernard, Case Narrative: Possible Chemical Warefare Agent Incident Involving a U.S. Marine, Last Update: Mar. 16, 2000, http://www.gulflink.osd.mil/injured_marine/index.htm.*

(Continued)

*Primary Examiner*—Sean Conley
*Assistant Examiner*—Regina Yoo
(74) *Attorney, Agent, or Firm*—Merchant & Gould P.C.

(57) ABSTRACT

A decontamination system suitable for decontaminating items of medical equipment such as endoscopes, the system comprising:
(I) a plurality of pre-clean wipes comprising moist fabric members for wiping an item to be decontaminated;
(II) a two-part sterilant system comprising:
  (a) a first part comprising a first reagent in a carrier medium; and
  (b) a second part which is miscible with the first part and which comprises a second reagent in a carrier medium;
wherein the first reagent and the second reagent will react when mixed to provide a sterilising composition;
the first part being contained in a dispenser (2) whereby it may be dispensed as a fluid, and the second part being absorbed or impregnated in a plurality of sterilising wipes (18) each of which comprises a fabric member in a sealed container (20); and
(III) a plurality of rinse wipes, each rinse wipe comprising a moist, sterile, fabric member in its own sealed container (40).

23 Claims, 8 Drawing Sheets

U.S. PATENT DOCUMENTS

| | | | |
|---|---|---|---|
| 4,689,215 A | | 8/1987 | Ratcliff |
| 4,705,461 A | | 11/1987 | Clements |
| 4,789,100 A | | 12/1988 | Senf |
| 4,789,166 A | | 12/1988 | Rericha et al. |
| 4,806,079 A | | 2/1989 | Kuhn |
| 4,832,580 A | | 5/1989 | Tsuyoshi et al. |
| 4,854,501 A | | 8/1989 | Ricci |
| 4,876,023 A | | 10/1989 | Dickenson et al. |
| 4,906,488 A | | 3/1990 | Pera |
| 4,940,701 A | | 7/1990 | Davis |
| 4,978,530 A | | 12/1990 | Strong |
| 5,002,204 A | | 3/1991 | Sakai |
| 5,091,107 A | | 2/1992 | Hutchings |
| 5,133,483 A | | 7/1992 | Buckles |
| 5,141,803 A | * | 8/1992 | Pregozen .................... 442/123 |
| 5,146,944 A | | 9/1992 | Waldrum |
| 5,152,461 A | | 10/1992 | Proctor |
| 5,197,636 A | | 3/1993 | Mitchell et al. |
| 5,204,081 A | | 4/1993 | Mason et al. |
| 5,213,884 A | * | 5/1993 | Fellows ...................... 442/263 |
| 5,224,627 A | | 7/1993 | Weag |
| 5,227,168 A | * | 7/1993 | Chvapil et al. .............. 424/445 |
| 5,337,929 A | | 8/1994 | van der Heijden |
| 5,388,761 A | | 2/1995 | Langeman |
| 5,425,815 A | | 6/1995 | Parker et al. |
| 5,518,675 A | | 5/1996 | Sims |
| 5,524,983 A | | 6/1996 | Dittgen et al. |
| 5,649,647 A | | 7/1997 | Kodarar |
| 5,673,821 A | | 10/1997 | Davis et al. |
| 5,696,046 A | | 12/1997 | Green |
| 5,702,992 A | * | 12/1997 | Martin et al. ............... 442/123 |
| 5,721,521 A | | 2/1998 | Drabeck et al. |
| 5,738,840 A | | 4/1998 | Richter |
| 5,766,333 A | | 6/1998 | Lukens |
| 5,783,146 A | | 7/1998 | Williams, Jr. |
| 5,895,638 A | | 4/1999 | Tenney |
| 5,958,536 A | * | 9/1999 | Gelsinger et al. .......... 428/40.1 |
| 5,985,302 A | * | 11/1999 | Dorr et al. .................. 424/404 |
| 6,007,772 A | | 12/1999 | Green |
| 6,013,614 A | * | 1/2000 | Mahdessian ................ 510/277 |
| 6,082,534 A | * | 7/2000 | Dotson ....................... 206/210 |
| 6,399,557 B2 | | 6/2002 | Perkins et al. |
| 6,431,189 B1 | | 8/2002 | Deibert |
| 6,484,879 B2 | | 11/2002 | Desmarais et al. |
| 6,566,318 B2 | | 5/2003 | Perkins et al. |
| 6,624,130 B2 | | 9/2003 | Giblin et al. |
| 6,651,848 B1 | | 11/2003 | Redmond |
| 6,669,387 B2 | | 12/2003 | Gruenbacher et al. |
| 6,696,047 B2 | * | 2/2004 | Scott et al. .................... 424/53 |
| 6,753,306 B2 | * | 6/2004 | Simpson ...................... 510/439 |
| 2002/0006887 A1 | | 1/2002 | Radwanski et al. |
| 2003/0068454 A1 | * | 4/2003 | Smith ......................... 428/35.2 |
| 2003/0180247 A1 | | 9/2003 | Morelli et al. |
| 2003/0216281 A1 | * | 11/2003 | DeLeo et al. ............... 510/475 |
| 2004/0109853 A1 | * | 6/2004 | McDaniel ................... 424/94.6 |
| 2004/0195824 A1 | * | 10/2004 | Blank ............................ 283/81 |
| 2005/0159063 A1 | * | 7/2005 | Hill et al. ..................... 442/327 |
| 2005/0210615 A1 | | 9/2005 | Shastry et al. |

FOREIGN PATENT DOCUMENTS

| | | | |
|---|---|---|---|
| DE | 41 34 494 | | 4/1993 |
| EP | 0 017 968 | | 4/1980 |
| EP | 0 081 017 | | 6/1983 |
| EP | 0 423 816 | | 4/1991 |
| EP | 0 423 817 | | 4/1991 |
| EP | 423817 A2 | * | 4/1991 |
| EP | 0 314 994 | | 10/1998 |
| EP | 1 310 263 | | 9/2001 |
| EP | 0 785 719 | | 1/2003 |
| EP | 1 340 511 | | 9/2003 |
| FR | 2 569 779 | | 3/1986 |
| GB | 2 004 475 | | 4/1979 |
| GB | 2 304 706 | | 3/1997 |
| GB | 2 329 589 | | 3/1999 |
| GB | 2329589 A | * | 3/1999 |
| JP | 2001 129041 | | 5/2001 |
| WO | WO 96/10916 | | 4/1996 |
| WO | WO 00/56203 | * | 9/2000 |
| WO | WO 00/76916 | | 12/2000 |
| WO | WO 01/37886 | | 5/2001 |
| WO | WO 01/64325 | | 9/2001 |
| WO | WO 03/000586 | | 1/2003 |

OTHER PUBLICATIONS

Abstract for JP 60 58147. Apr. 4, 1985.
Abstract for JP 7 1828. Jan. 20, 1995.
Office Action for co-pending U.S. Appl. No. 10/935,651.
Beeby et al., "A bacterial spore test piece for the control of ethylene oxide sterilization," *J. Appl. Bact.* (1965) 28 (3): 349-360.
Hooper, P., "Decontamination—Machinery and Testing," *ISSM Journal* (2000) 5 (1): 4-8.
"Washer-disinfectors—Validation and verification," *Health Technical Memorandum* 2030 (1997): 1-163.

* cited by examiner

Tristel Sterilising Wipe Quality Audit Trail

| Device Being decontaminated | | | Pre-Cleaning Method | | Sterilising Traceability label | | Activation | Rinsing Method | | Destination of device | | Confirmation By person responsible |
|---|---|---|---|---|---|---|---|---|---|---|---|---|
| Item | Ref. no. | | Tristel Pre-Clean Wipe | YES | Record Book Label Tristel Sterilising Wipes | YES | | Tristel Rinse Wipe | YES | Patient | YES | This device has been decontaminated and is prepared and ready for use. |
| ENDOSCOPE | 0110 3 | | Other | | Lot No. 000001 Use before 1/12/2004 Activator Lot No. | | | Other | | Storage | | Name α. RUSSELL |
| Patients I.D 03013510 | | | | | | | | | | If stored, affix Patient's Notes Label from sachet here | | Signed |
| Date 10/3/04 | Time 11.45 | | | | | | | | | | | |

| Device Being decontaminated | | | Pre-Cleaning Method | | Sterilising Traceability label | | Activation | Rinsing Method | | Destination of device | | Confirmation By person responsible |
|---|---|---|---|---|---|---|---|---|---|---|---|---|
| Item | Ref. no. | | Tristel Pre-Clean Wipe | YES | Record Book Label Tristel Sterilising Wipes | YES | | Tristel Rinse Wipe | YES | Patient's Notes Label Tristel Sterilising Wipes | YES | This device has been decontaminated and is prepared and ready for use. |
| ENDOSCOPE | 0110 3 | | Other | | Lot No. 000001 Use before 1/12/2004 Activator Lot No. | | | Other | | Lot No. 000001 Use before 1/12/2004 Activator Lot No. | | Name α. RUSSELL |
| Patients I.D | | | | | | | | | | | | Signed |
| Date 10/3/04 | Time 11.45 | | | | | | | | | | | |

| Device Being decontaminated | | | Pre-Cleaning Method | | Sterilising Traceability label | | Activation | Rinsing Method | | Destination of device | | Confirmation By person responsible |
|---|---|---|---|---|---|---|---|---|---|---|---|---|
| Item | Ref. no. | | Tristel Pre-Clean Wipe | | Tristel Sterilising Wipe | | | Tristel Rinse Wipe | | Patient | | This device has been decontaminated and is prepared and ready for use. |
| | | | Other | | Affix Record Book Label from sachet here | | | Other | | Storage | | Name |
| Patients I.D | | | | | | | | | | If stored, affix Patient's Notes Label from sachet here | | Signed |
| Date | Time | | | | | | | | | | | |

| Device Being decontaminated | | | Pre-Cleaning Method | | Sterilising Traceability label | | Activation | Rinsing Method | | Destination of device | | Confirmation By person responsible |
|---|---|---|---|---|---|---|---|---|---|---|---|---|
| Item | Ref. no. | | Tristel Pre-Clean Wipe | | Tristel Sterilising Wipe | | | Tristel Rinse Wipe | | Patient | | This device has been decontaminated and is prepared and ready for use. |
| | | | Other | | Affix Record Book Label from sachet here | | | Other | | Storage | | Name |
| Patients I.D | | | | | | | | | | If stored, affix Patient's Notes Label from sachet here | | Signed |
| Date | Time | | | | | | | | | | | |

DECONTAMINATION SYSTEM

FIELD OF THE INVENTION

The present invention relates to a decontamination system, notably to a system for ensuring that a medical device is made safe after use on one patient prior to use on another patient. The invention preferably makes use of chlorine dioxide ($ClO_2$) as a sterilant.

BACKGROUND TO THE INVENTION

"Traditionally, the word 'decontamination' has been applied to those cleaning procedures—automatic and/or manual—that take place prior to sterilisation. Recent documentation, however, has redefined the word to apply to the whole series of procedures to ensure that a device is made safe after use on one patient prior to use on a second. Decontamination can thus include cleaning, disinfecting and sterilising." This statement is taken from an article published in the ISSM (Institute of Sterile Service Managers) Journal, Vol. 5, No. 1 July-September 2000. The statement helps to explain what the decontamination process has come to mean in modern UK hospitals and goes on to refer to HTM2030, which has been the driver for change in processing many types of medical instruments. The term 'decontamination' will be used herein to refer to the above redefinition, including cleaning and sterilising.

Health Technical Memorandum (HTM) 2030 was introduced in 1993 and updated in 1997 and 2001 to improve the sterile processing performance of washer disinfectors. HTM2030 addresses the use of washer-disinfectors for instruments, many of which cannot be autoclaved, for example flexible endoscopes. In essence, it describes the need to wash instruments thoroughly before disinfection/sterilisation (by heat or by chemical); to be followed by the disinfection/sterilisation stage and to culminate, in the case of chemical disinfection, in the rinsing of the instrument. HTM2030 also addresses the need for the entire process to be recorded in a traceability and audit system.

Two-part sterilising solutions are used in applications where the active sterilising ingredient is unstable over time. The solution is therefore prepared in situ shortly before it is to be used. A particularly important sterilising agent is chlorine dioxide, which may be formed from mixtures of various reagents including: chlorite and acid; chlorate, peroxide and acid; and chlorite, hypochlorite, and a suitable buffer. Chlorine dioxide has excellent sterilising and bactericidal properties, and oral ingestion in man and animals has been shown to be relatively safe.

The cleaning of endoscopes and other medical equipment with suitable chlorine dioxide solutions is known. See, for example, European Patent Number 0 785 719 and U.S. Pat. Nos. 5,696,046 and 6,007,772, the contents of which are hereby incorporated by reference.

It is not always convenient to mix up batches of solutions for use in sterilising equipment. For wiping down (rather than thoroughly cleaning inside and out) of endoscopes and probes, wipes of alcohol, general-purpose detergent, or soapy water are generally used, but these are not as effective as chlorine dioxide. It is desirable to be able readily to make up small quantities of two-component sterilising agents when desired and to be able to make such agents up in a form in which they may be readily handled for a particular application. It is particularly desired to provide a decontamination system which meets the HTM2030 standard.

SUMMARY OF THE INVENTION

According to a first aspect of the present invention there is provided a decontamination system suitable for decontaminating items of medical equipment such as endoscopes, the system comprising:
(I) a plurality of pre-clean wipes comprising moist fabric members for wiping an item to be decontaminated;
(II) a two-part sterilant system comprising:
   (a) a first part comprising a first reagent in a carrier medium; and
   (b) a second part which is miscible with the first part and which comprises a second reagent in a carrier medium;
   wherein the first reagent and the second reagent will react when mixed to provide a sterilising composition;
   the first part being contained in a dispenser whereby it may be dispensed as a fluid, and the second part being absorbed or impregnated in a plurality of sterilising wipes each of which comprises a fabric member in a sealed container; and
(III) a plurality of rinse wipes, each rinse wipe comprising a moist, sterile, fabric member in its own sealed container.

The system enables an item such as a flexible endoscope to be decontaminated without the use of a conventional washer-disinfector and, indeed, without a water supply.

Each of the three wipes performs one stage of the decontamination process. The chemistry of the rinse wipe may be tailored or selected to give optimal surface rinsing for a given sterilant system. For example, the rinse wipe may include an agent for neutralising an active ingredient of the sterilant system ('sterilising wipe'). In a preferred embodiment the sterilising wipe has $ClO_2$ as the active ingredient and the rinse wipe contains an antioxidant such as sodium thiosulphate for neutralising excess of $ClO_2$.

In prior art decontamination processes, ie, in washer-disinfectors, which use filtered mains water or water produced by reverse osmosis, or in a manual procedure in which tap water or bottled sterile water may be used, the water is indiscriminate to the chemistry employed in the disinfection process. Consequently the sterilant may be insufficiently removed by rinsing, or an undesirable excess of rinse water may be required.

The fabric members may be formed from any suitable fabrics, either woven or non-woven. They may be of natural or man-made fibres, for example polyester, cotton, cellulose or mixtures thereof. Other suitable fabrics will be well known to those skilled in the textile or fabric arts. The fabric members for each of the three types of wipe may be same or different from each other.

Pre-Clean Wipe

The pre-clean wipe is moist and preferably provided in a sealed container. The container may be resealable, for example a canister with a lid, or a resealable sachet. In a preferred embodiment, each pre-clean wipe is provided in its own sachet which may be factory-sealed and disposed of after use.

It is preferred that the pre-clean wipe contain additional components to improve its efficiency. The wipe may contain at least one surfactant to promote wetting and/or dissolution of organic deposits. The surfactant may be a foaming surfactant such as a detergent or a soap, or a low-foam non-ionic surfactant such as Lanawet LF-6. The pre-clean wipe may advantageously contain other agents, for example one or more selected from the following: enzymes for digesting or solubilizing organic deposits, humectants, buffers, preservatives, corrosion inhibitors, solvents, or anti-foaming agents.

Sterilant System

The term 'fluid' is used herein to include liquids, foams, sprays, pastes, aerosols, powders, sols and gels. It is particularly preferred that the first part of the sterilant system is dispensed as a foam or a spray to facilitate its coverage of a desired area of the fabric member. Optionally, the dispenser may have a relatively large dispensing head, for supplying the fluid over all or a substantial part of a surface of the fabric member. For example, the dispensing head may take the form of a rose or sprinkler with a multitude of small orifices to spread the fluid over the fabric member.

The dispenser is preferably a pump-dispenser, notably a trigger-operated dispenser, both for convenience and to facilitate the dispensing of metered quantities. However, other pump dispensers could be used, for example, a squeeze bottle with a suitable spray or foam nozzle. The invention will, for convenience, be described hereinafter with reference to the use of a trigger-operated dispenser, but it is to be understood that it is not limited to this embodiment.

By putting up the first part in a trigger-operated dispenser, small quantities may be readily dispensed without risk of spillage. Preferably the dispenser comprises a sprayer apparatus that provides the first part as a foam so that it is at least partly form-retaining and can be readily seen and manipulated. We have also found that providing the first part in a foam may have the beneficial effect of reducing the odour of chlorine dioxide when the wipe is activated. The invention will for convenience be described with reference to this preferred embodiment, but it will be understood that the invention is not limited to this embodiment.

The trigger sprayer may include a mixing chamber to facilitate mixing of the first part with air, for example as described in U.S. Pat. No. 5,337,929.

By providing the second part absorbed in a fabric wipe, a sterilising wipe may readily be prepared by applying the first part to the fabric wipe. The user may fold the wipe or rub two halves together to facilitate mixing. The wipes are particularly useful for cleaning, disinfecting, and sterilising surfaces and equipment, notably in a medical environment.

The first part may include a coloured component so that a visual indication of the coverage of the wipe with the first part can be made.

In a preferred embodiment, at least one of the first and second parts is provided with an indicator reagent that changes colour to show that sufficient mixing has taken place. Where the first part and the second part are of different pH, the indicator may be a pH-sensitive indicator. Suitable indicators are well known to those skilled in the art, non-limiting examples including: phenol red, litmus, thymol blue, pentamethoxy red, tropeolin OO, 2,4-dinitrophenol, methyl yellow, methyl orange, bromophenol blue, tetrabromophenol blue, alizarin sodium sulphonate, α-naphthyl red, p-ethoxychrysoidine, bromocresol green, methyl red, bromocresol purple, chlorophenyl red, bromothymol blue, p-nitrophenol, azolitmin, neutral red, rosalic acid, cresol red, α-naphtholphthalein, tropeolin OOO, phenolphthalein, α-naphtholbenzein, thymolphthalein, nile blue, alizarin yellow, diazo violet, tropeolin O, nitramine, Poirrer's blue, trinitrobenzoic acid, and mixtures thereof. It is preferred that the indicator is selected so that both parts are separately colourless and the colour develops when the two parts are mixed.

Alternatively, or additionally, one or more fluorescent additives may be included so that the mixture fluoresces to indicate mixing. Non-limiting examples of suitable fluorescing agents include: 4-methylumbelliferone, 3,6-dihydroxanthone, quinine, thioflavin, 1-napthol, harmine, coumarin, acridine orange, cotarmine, and mixtures thereof.

The indicator (colour change or fluorescent) may be included in either part. Preferred proportions by weight are about 0.1 to 10%, notably about 0.5 to 2%.

The carrier mediums may be fluids such as liquids or sols, or they may be more form-retaining or viscous compositions such as gels or pastes. It is preferred that at least one reagent is present in an aqueous fluid, although other additives may of course be present. Preferably both reagents are put up in aqueous fluids.

The trigger-operated dispenser may be a conventional atomizer or foamer, or other manual pump in which the contents are expelled manually by operation of the trigger by the user. Alternatively, the dispenser may contain a propellant to dispense the contents when operation of the trigger opens a valve, as is well known in applications such as shaving foam canisters and the like. Suitable dispensers will be well known to those skilled in the art.

The preferred sterilising agent is chlorine dioxide, which may be formed from suitable known reagents. In a preferred embodiment one reagent is a chlorite (notably sodium chlorite) and the other is an acid, preferably with a buffer. Suitable acids include lactic acid, citric acid, boric acid, phosphoric acid, acetic acid, sorbic acid, ascorbic acid, hydrochloric acid or mixtures thereof. In a preferred embodiment a mixture of acids is used, notably a mixture of citric, sorbic and boric acids.

A particularly preferred system is as described in EP 0 785 719, with the corrosion inhibitors optionally not included, and with other additives as desired for particular applications. In addition to suitable indicators, optional additives include foam-promoting agents or stabilizers, humectants, essential oils and fragrances. Other sterilising agents may also be employed; for example chlorine or oxygen. Chlorine may be produced by reaction between a hypochlorite such as sodium hypochlorite, and a suitable acid or buffer. Oxygen may be produced by reaction between a peroxide and a catalyst such as catalase, optionally in the presence of a buffer. For convenience hereinafter, the invention will be described with reference to chlorine dioxide as the sterilising agent.

Suitable foam promoters will be well known to those skilled in the art. Non-limiting examples include: sodium laureth sulphate, ammonium lauryl sulphate, cocamide DEA, cocamidopropyl betaine, sodium lauryl sarcosinate, cocamidopropylamine oxide, monoethanolamine lauryl sulphate, cocamidopropyl hydroxysultaine, cocoyl sarcosinate. Anionic, cationic, non-ionic and amphoteric surfactants may be employed depending on the chemistry of the reagents. The foam promoters are selected to provide a stable foam structure. The foam promoter may comprise from about 0.1 to 50% by weight of the first part, notably from about 1 to 10%, preferably from about 3 to 6%.

Suitable foam stabilizers well known to those skilled in the art may also be used, in proportions similar to those for the foam-promoters. Non-limiting examples include: alkanolamides, for example monoethanolamides and diethanolamides, amine oxides, betaines, protein hydrolysates and cellulose derivatives such as carboxymethylcellulose.

In a preferred embodiment, a humectant is included in at least one of the first and second parts. Humectants serve to reduce the rate of evaporation of components and improve product feel if direct skin contact is involved. We have found that the use of a humectant reduces the volatility of chlorine dioxide, which reduces the odour of chlorine dioxide and prolongs the life of the activated mixture. Non-limiting examples of suitable humectants include sodium lactate and polyols, for example glycerine, sorbitol, propylene glycol, diethylene glycol and ethylene glycol. The humectant may be present in any desired amount, particularly from about 0.1 to 50% by weight, notably from about 0.5 to 10%, preferably from about 1 to 3%.

Where one of the reagents is basic or oxidising, for example sodium chlorite, it is particularly preferred that this reagent is provided in the trigger dispenser rather than in the wipe, because such reagents may react with the fabric over time. Preferably the optional humectant is included in the first part, with the sodium chlorite or other first reagent.

The first and/or second part may further include a biocide to ensure that, in the event of poor mixing of the parts, a biocidal effect is still present. The first and/or second part may also include a preservative.

Equal weights of the first part and the second part may provide, when mixed, a sterilising composition having a pH of from 1.0 to 10.5, but it is preferred that the composition has a pH of from 4.5 to 6.5 as this may result in a more stable compound.

A plurality of fabric members may be provided in a single resealable container, for example a canister with a lid, or a resealable sachet. In a preferred embodiment, each fabric member is provided in its own sachet which may be factory-sealed and disposed of after use. In a particularly preferred embodiment, each sealed sachet contains a single fabric wipe and carries a removable adhesive label on its outer surface, the label containing information about the provenance of the wipe, for example its lot or batch number, its date of manufacture, or its expiry date. The label may be affixed to a record sheet and used as part of an audit trail to provide a record that an item of equipment has been properly decontaminated and the date on which this was done. In one embodiment the label adhesive and the record sheet are selected so that, though the label is releasably adhered to the sachet, it will become permanently adhered to the record sheet and cannot be removed intact. This arrangement helps provide a permanent validation record of the decontamination process. The record sheet may be provided in any convenient form, for example as a single sheet, as part of a loose-leaf binder, or in an audit trail book.

It will be understood that the sterilant system may optionally be provided as a stand-alone sterilant system, for use without the pre-clean wipe or the rinse wipe, or for use as a replacement component in the decontaminant system.

Rinse Wipe

To maintain sterility of the wipes it is preferred that each fabric member is provided in its own sachet which is factory-sealed and disposed of after use. The sachets may be gamma-irradiated before or after sealing to ensure sterility.

In addition to water (preferably deionised water), optional components may comprise an antioxidant to neutralise oxidant in the sterilant system, a sequestering agent to sequester metal salts and improve cleaning, and a lubricant to provide visual enhancement, or 'shine' to a decontaminated item such as an endoscope. A preservative may optionally be included, to eliminate toxic residues and enhance product stability prior to gamma-irradiation.

Other aspects and benefits of the invention will appear in the following specification, drawings and claims.

BRIEF DESCRIPTION OF THE DRAWINGS

The invention will now be further described, by way of example, with reference to the following drawings in which:

FIG. 9 shows a record sheet for use with the decontamination system of FIG. 5 in accordance with a further embodiment of the invention.

DETAILED DESCRIPTION

Figure 1:
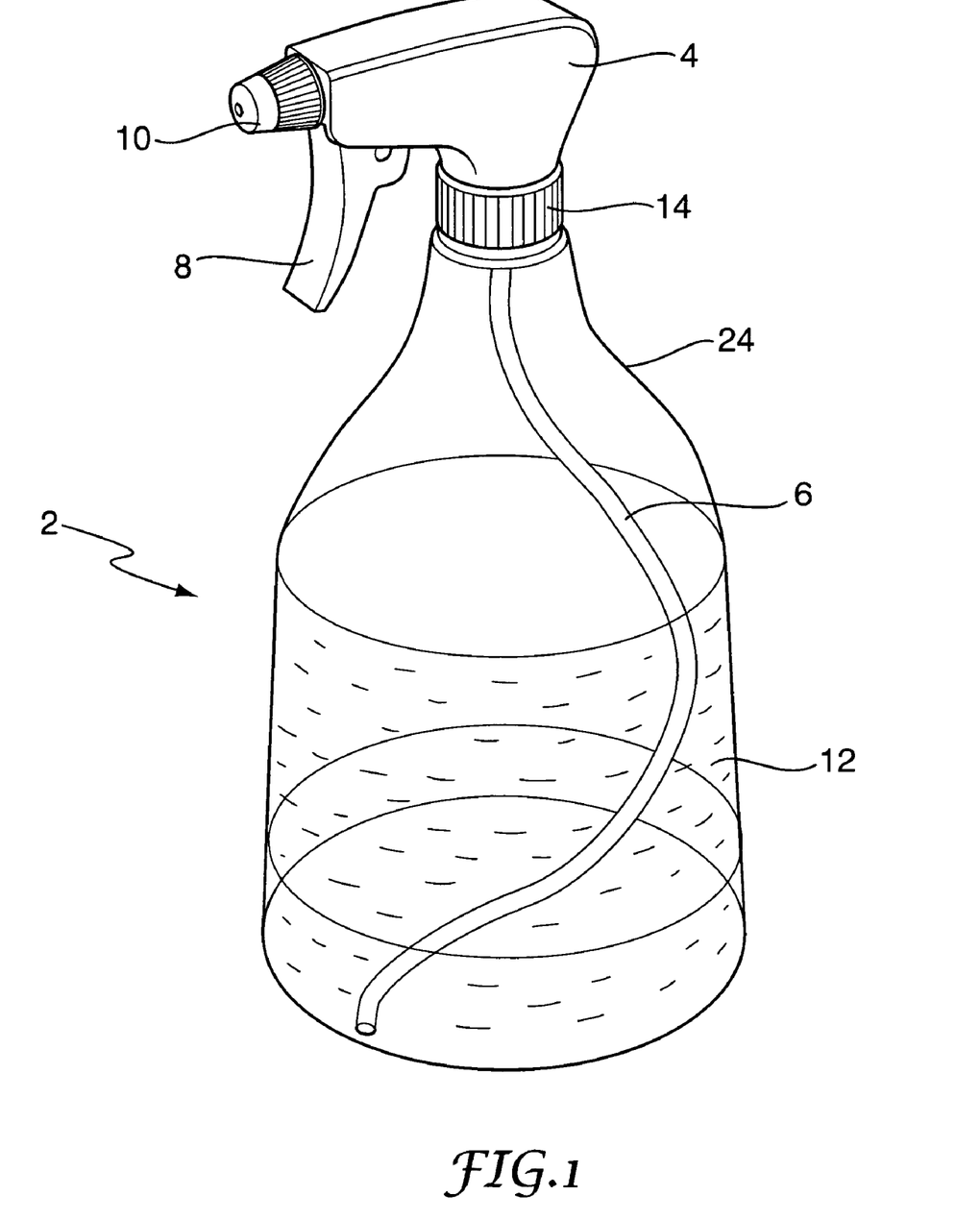
FIGS. 1 and 3 show views of alternative embodiments of pump dispensers for use in a decontamination system in accordance with embodiments of the present invention.

The pump dispenser 2 shown in FIG. 1 is a trigger sprayer of a construction well known per se. The dispenser 2 comprises a body 24 connected to a sprayer head 4 by an internally screw-threaded connector ring 14. A spray nozzle 10 in the head is connected to an aqueous liquid 12 by means of a dip tube 6. A user dispenses the liquid 12 through the nozzle 10 by operation of a trigger 8. Rotation of the nozzle allows the user to dispense the fluid as either a spray of fine droplets or as a foam.

In the present example, the liquid 12 (first part) comprises 0.75% of a first reagent (sodium chlorite), 3.0% foam promoter (Cocamidopropyl Betaine). The remainder is deionised water. In this specification, all parts are by weight unless otherwise indicated. Operation of the trigger 8 dispenses the first part 12 as a foam.

Figure 3:
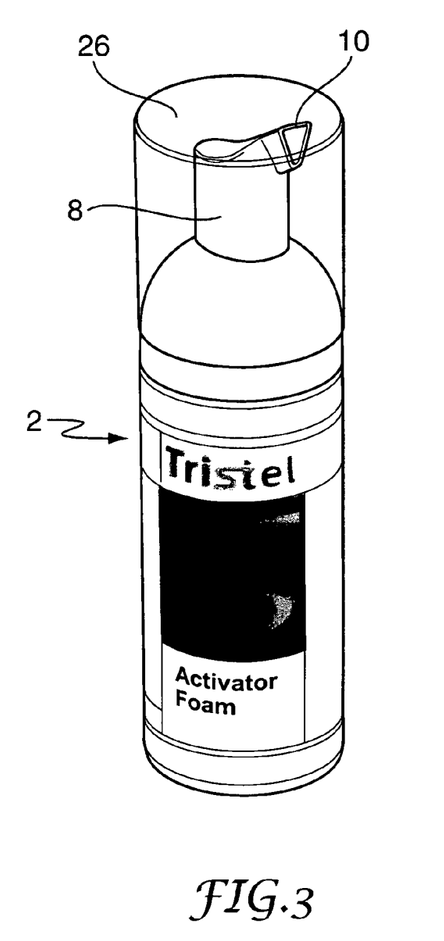

An alternative design of pump dispenser 2 is illustrated in FIG. 3. The trigger 8 is formed integrally with the nozzle 10. Depressing the trigger 8 dispenses a portion of the fluid contents as a foam (referred to as the 'Activator Foam' because it activates the sterilising powers of a sterilising wipe). A protective cap 26 is provided to cover the nozzle 10 and trigger 8 when not in use.

Figure 2:
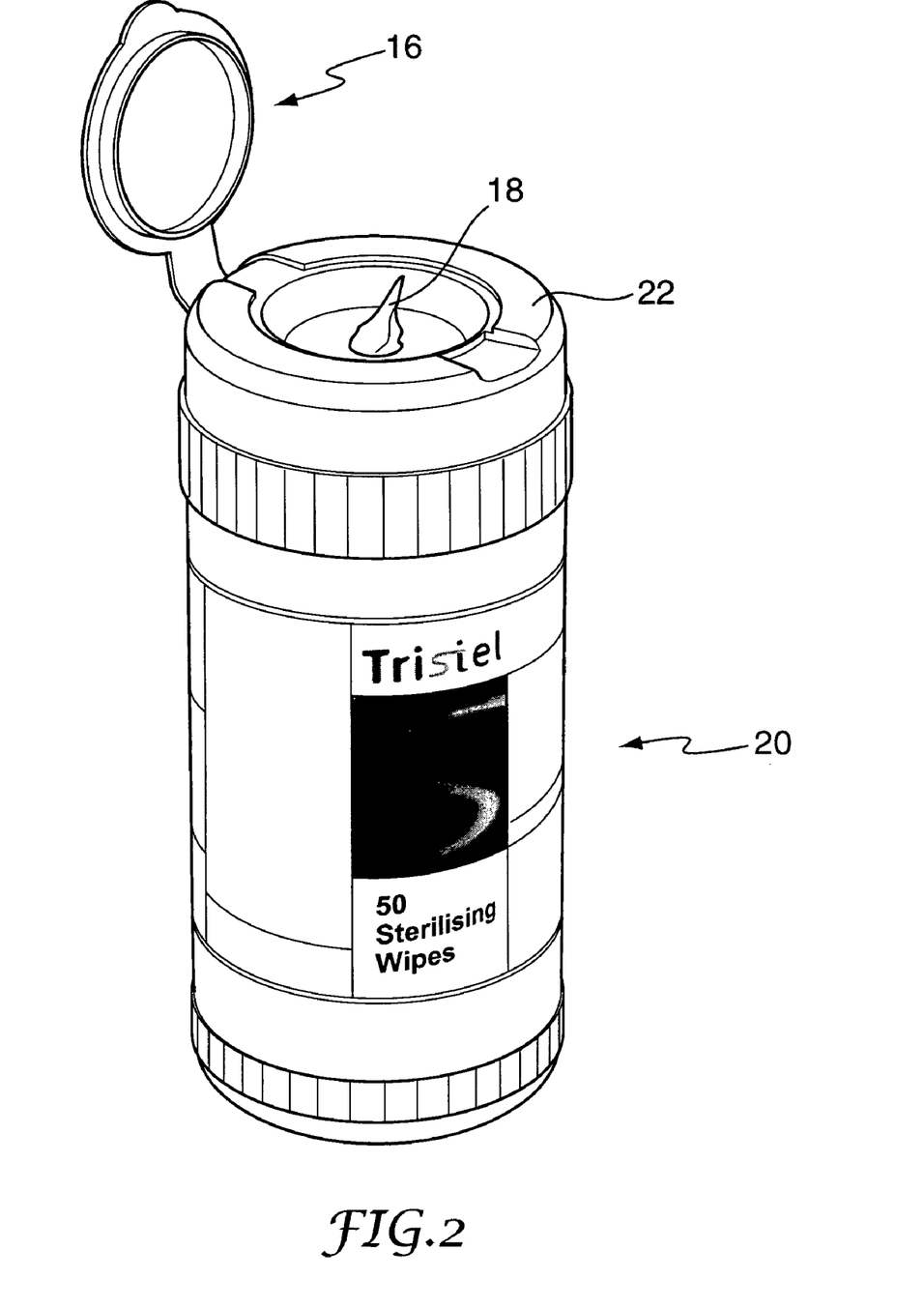
FIGS. 2 and 4 are perspective views of a canister of sterilising wipes for use in a decontamination system in accordance with embodiments of the present invention.
Figure 4:
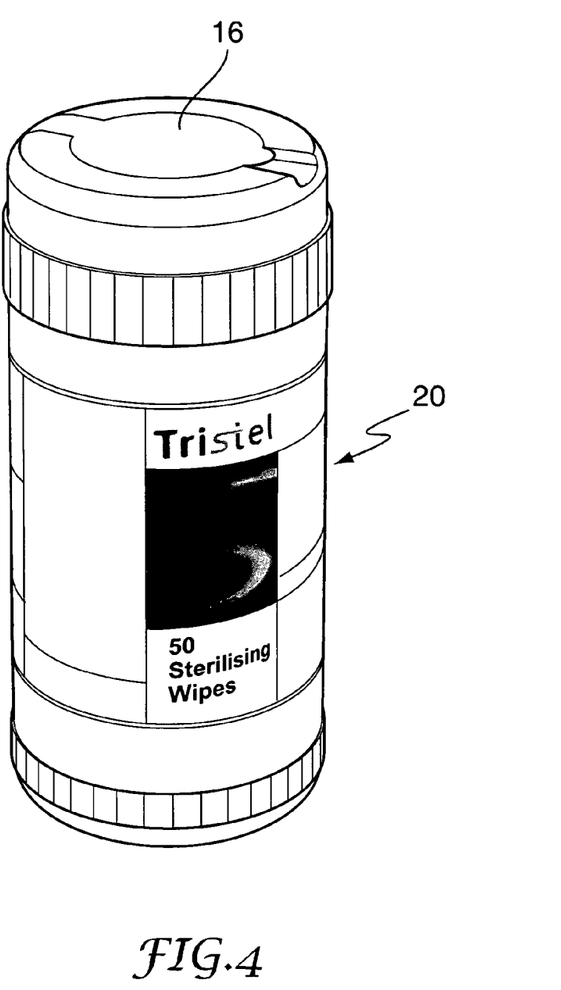
Figure 5:
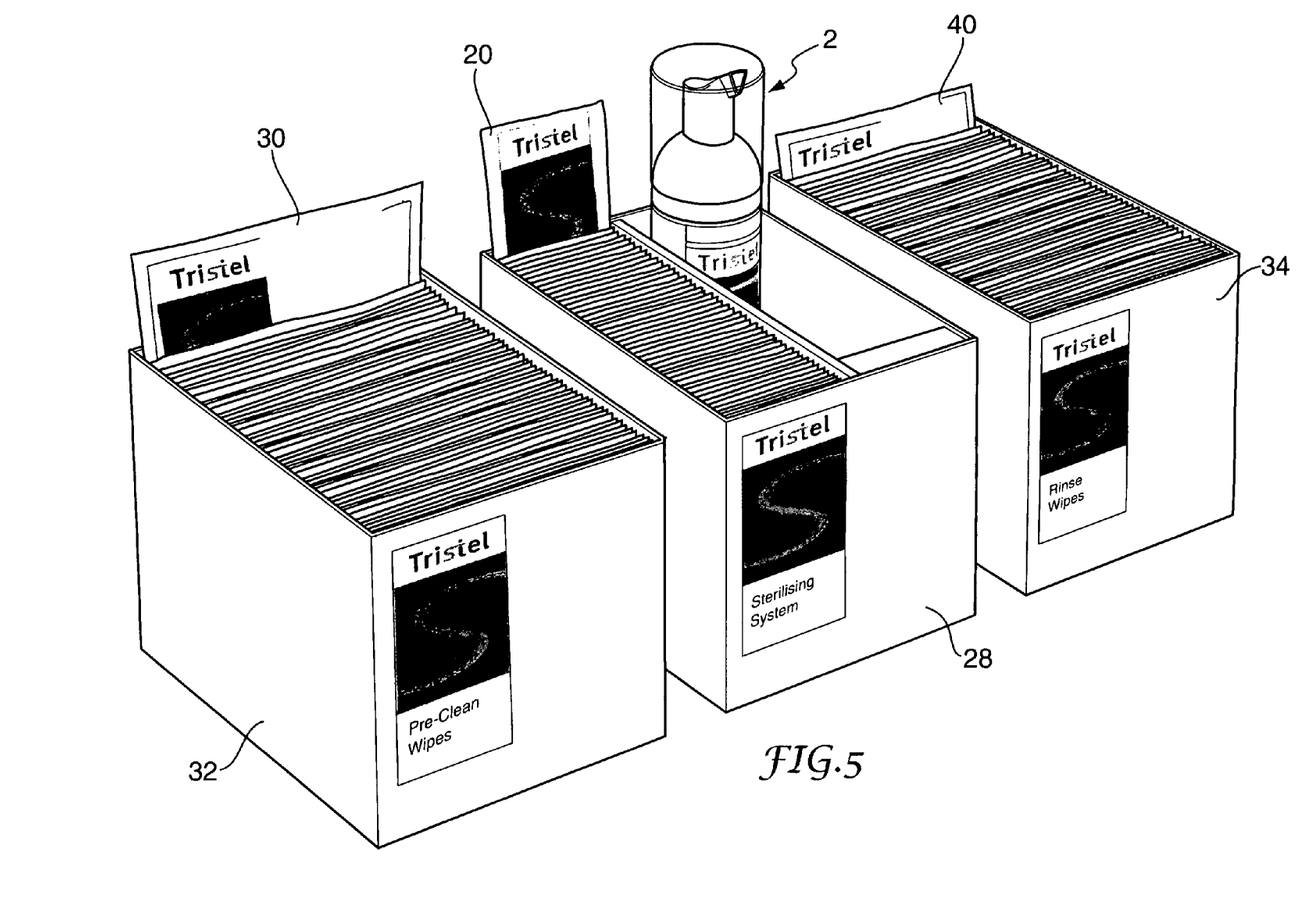
FIG. 5 shows a decontamination system in accordance with another embodiment of the invention.

Turning now to FIGS. 2 and 4, a sealable container 20 is also of a construction well known per se. The container 20 is a hollow cylinder fitted with a cap 22. The container 20 contains a roll of interleaved fabric sheets (or 'sterilising wipes') 18. In this example, the fabric sheets 18, are to be used as sterilising wipes, but it will be understood that the sheets 18 could also be used for other applications such as biocidal wound-dressings.

The cap 22 has a central opening through which a tip of the central wipe 18 is disposed. By pulling the central wipe 18, a user may remove this wipe from the container, leaving the next wipe in its place. A stopper 16 is provided on the cap 22 for releasably sealing the container 20.

In this example, the wipes 18 are impregnated with an aqueous acid solution (second part). In this example, the acid solution comprises 0.5% citric acid, 0.05% sorbic acid, 0.05% boric acid. The solution also comprises 0.35% of a buffer (trisodium phosphate). The solution also comprises 0.25% trisodium citrate, 1.0% glycerine, 0.1% benzotriazole, 0.1% sodium molybdate and 0.3% sodium nitrate. The remainder is deionised water.

The pump dispenser 2 and container 20 together comprise the sterilant system. To activate a sterilising wipe, a user removes the wipe 18 from the container 20, and applies a portion of foam from the dispenser 2 to the wipe 18. To facilitate mixing of the reagents in the foam and the wipe, the user may fold the wipe in half and crush or rub the folded wipe before opening it out. Preferably, one of the components is provided with a pH-sensitive indicator which changes colour or becomes coloured when adequate mixing has occurred, thereby indicating that sufficient $ClO_2$ has been generated in the wipe.

Once the sterilising wipe has been activated, it may be used for a number of applications, including wiping surfaces and sterilising medical equipment such as endoscopes.

The sterilant system illustrated in FIGS. 1-4 may be accompanied by a plurality of pre-clean wipes and a plurality of rinse wipes for treatment of an item to be decontaminated respectively before and after treatment with a sterilising wipe. Each wipe may be made from the same fabric and may have the same dimensions. All of the wipes may be identical except for the fluid with which they are impregnated or soaked.

In the preferred embodiment illustrated in FIGS. 5-8, each sterilising wipe is provided in its own sealed container 20, in this example a sachet. The disinfectant system comprises a box 32 of pre-clean wipes in sachets 30, a box 28 of sterilising wipes in sachets 20, and a box 34 of rinse wipes in sachets 40. Each sachet 20, 30, 40 is factory-sealed and may be disposed of after the wipe has been removed. The foam pump dispenser 2 is also provided in the box 28 of sterilising wipe sachets 20

Figure 6:
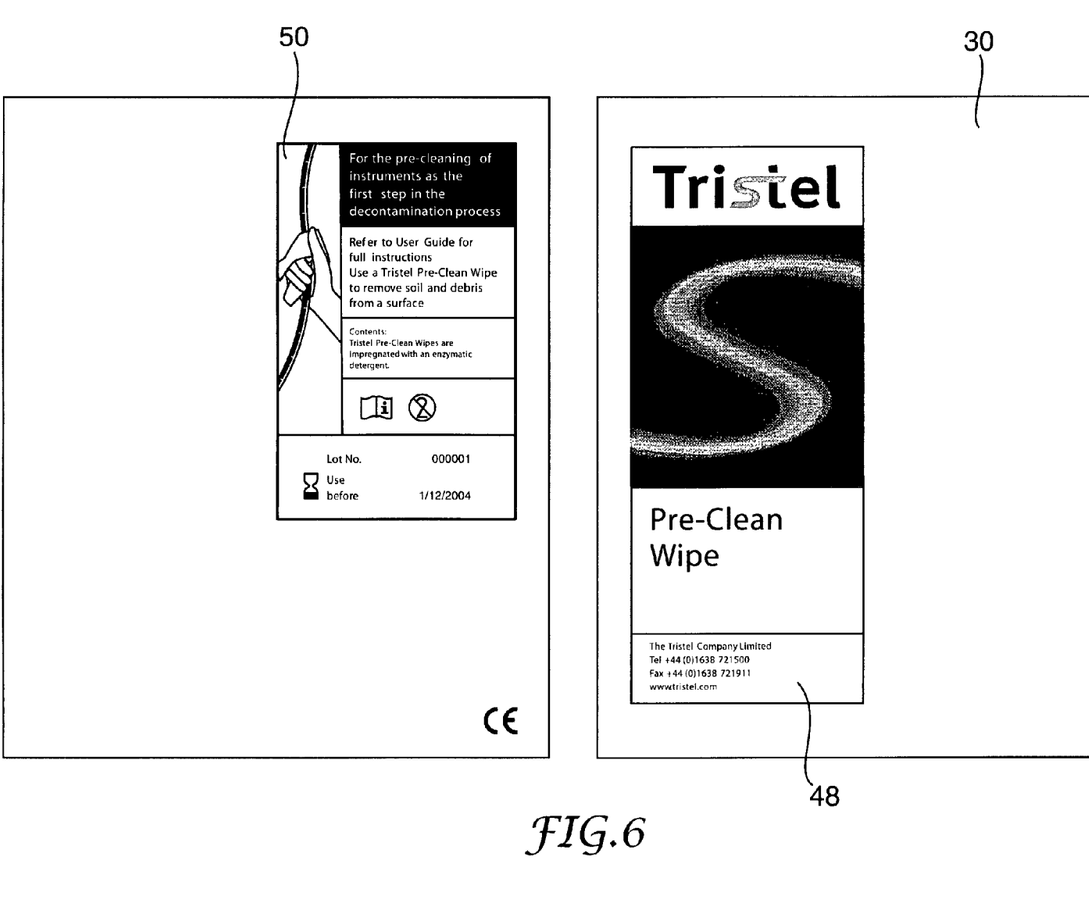
FIGS. 6 to 8 illustrate sachets from the system of FIG. 5.
Figure 7:
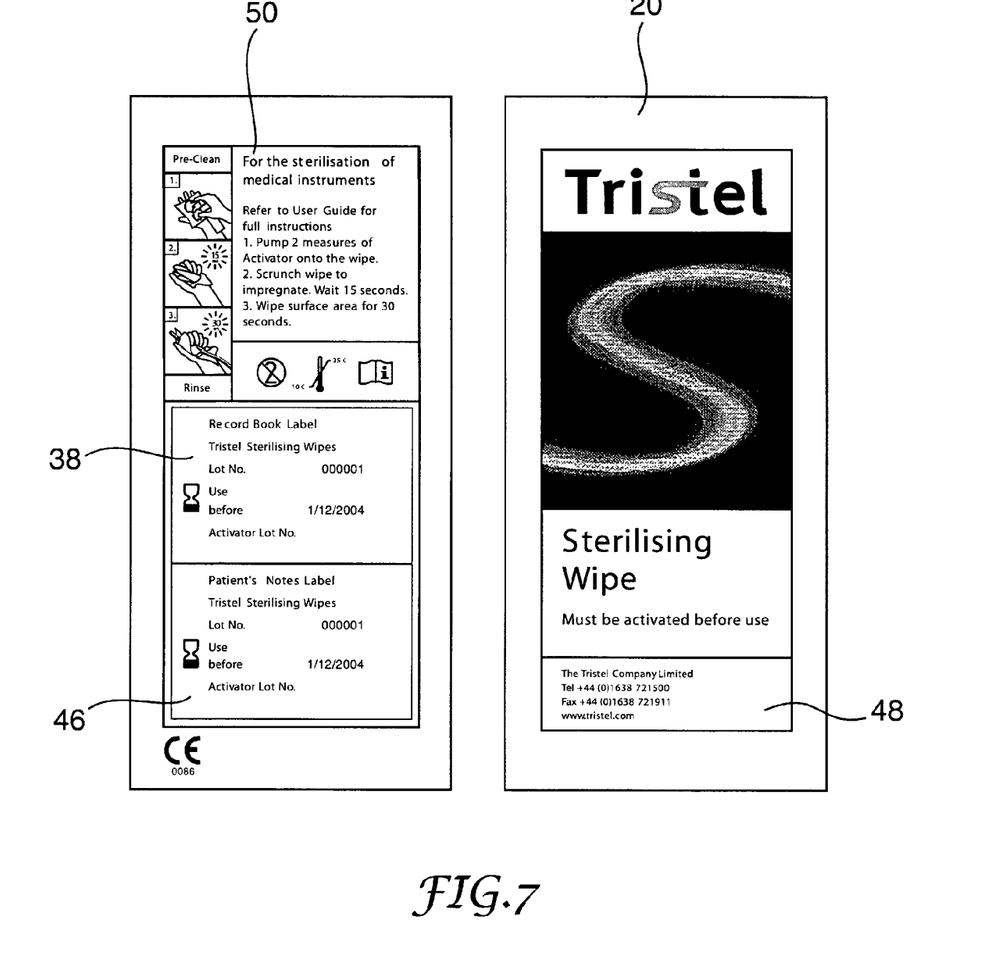
Figure 8:
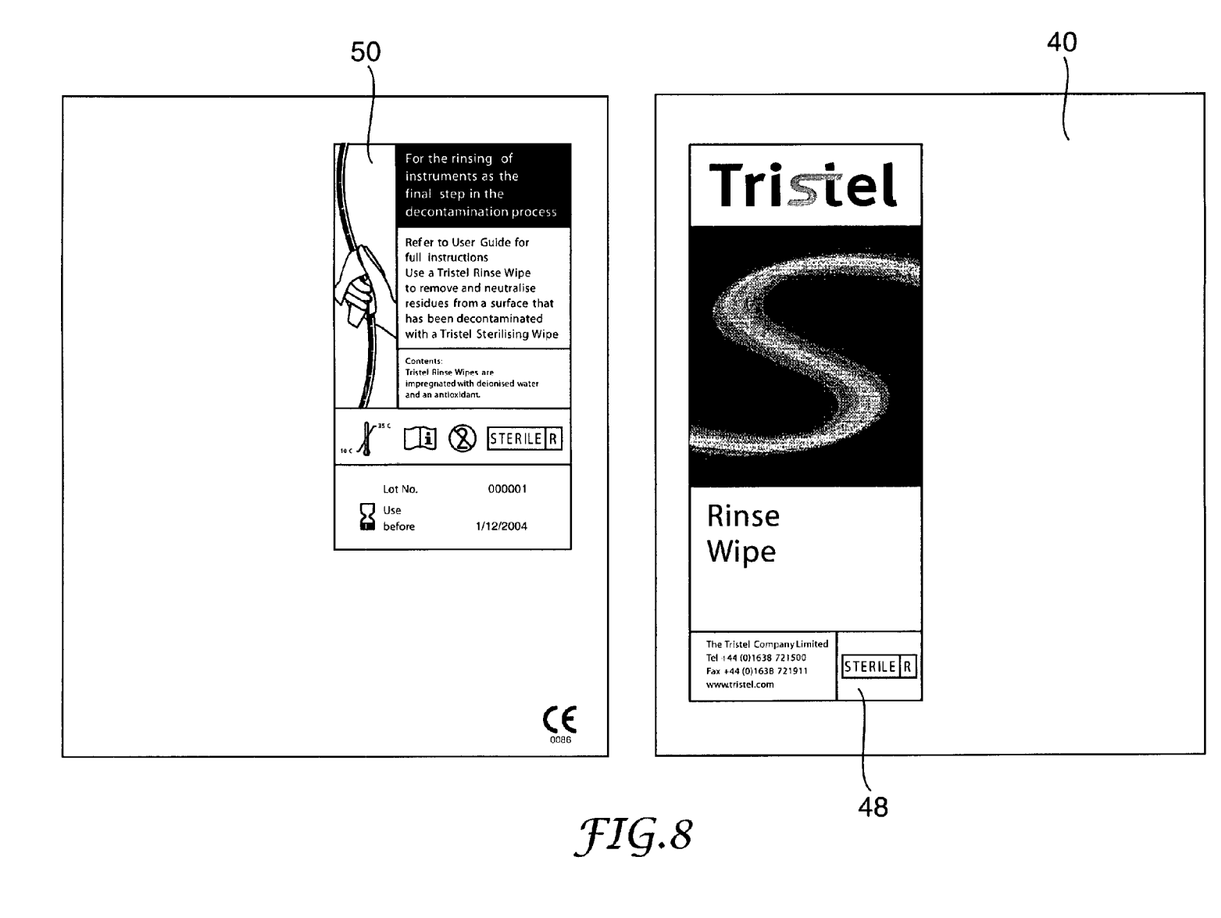

Each sachet 20, 30, 40 is provided with a label 48 on the front, identifying what the relevant wipe is for. A label 50 on the back gives information about how the wipe is to be used and other product details.

In this example, the pre-clean wipes contain the fluid formulation set forth in Table 1.

TABLE 1

| Ingredients | % w/w | CAS No. |
| --- | --- | --- |
| Deionised water | 93.285 | 7732-18-5 |
| Trisodium citrate | 0.5 | 68-04-02 |
| Sodium benzoate | 0.2 | 532-32-1 |
| Isopropanol | 1.5 | 67-63-0 |
| Monopropylene glycol | 3.0 | 57-55-06 |
| Glycol ethers (Downal DDNP grade) | 1.0 | 029911-27-1 |
| Alcalase | 0.2 | 9014-01-1 |
| Termamyl | 0.02 | 9000-90-2 |
| Lipolase | 0.02 | 9001-61-1 |
| Surfactant LF6 (low-foam) | 0.1 | 107600-33-9 |
| Phenoxyethanol (preservative) | 0.15 | 26172-55-4 |
| Silicone emulsion (antifoamer) | 0.025 | |

The trisodium citrate functions as a buffer; sodium benzoate functions as a preservative and corrosion inhibitor; monopropylene glycol functions as a humectant and solubiliser; the enzymes promote digestion and solubilizing of organic deposits.

The fluid formulation for the rinse wipes is given in Table 2.

TABLE 2

| RINSE WIPE FORMULATION | | |
| --- | --- | --- |
| Ingredients | % w/w | CAS No. |
| Deionised water | 97.25 | 7732-18-5 |
| Sodium thiosulphate | 0.5 | 7772-98-7 |
| EDTA (sodium salt) | 0.1 | 139-33-3 |
| Silicone emulsion (Dow 365) | 2.0 | |
| Phenoxyethanol (preservative) | 0.15 | 26172-55-4 |

Sodium thiosulphate is an antioxidant which helps to remove traces of $ClO_2$ from an item that has been sterilised. EDTA sodium salt is a sequestrant for removing dissolved metal salts and improving cleaning. The silicone emulsion functions as a lubricant to help 'shine' an item such as an endoscope and provide visual enhancement. The preservative is added before the rinse wipes are gamma-irradiated, to help reduce or eliminate toxic residue and enhance product stability prior to irradiation.

To decontaminate an item (in this example an endoscope), a user first opens a pre-clean wipe sachet 30 and takes out the pre-clean wipe. This wipe is used to remove soil and debris from the surface of the endoscope, in accordance with instructions on the label 50 of the sachet 30. After pre-cleaning, the pre-clean wipe is disposed of, and the user activates a sterilising wipe 18 by removing it from its sachet 20 and applying a metered dose of foam from the dispenser 2 (in this example, two measures of foam activator are applied in accordance with instructions on the label 50 on the back of the sachet 20). After manipulating the wipe 18 to ensure mixing of the activator foam and the fluid in the wipe 18, the user waits about 15 seconds and then wipes the surface of the endoscope for about 30 seconds. Finally, a rinse wipe sachet 40 is opened and a rinse wipe is used to wipe down the surface of the endoscope. The endoscope is now decontaminated and ready for use.

Referring now to FIG. 9, a record sheet 36 is illustrated for use in providing a quality audit trail for an item of equipment decontaminated with an embodiment of the system of the present invention. The record sheet 36 may be loose or it may be bound in a book or file. The record sheet carries boxes or other defined locations for recordal of information relating to the decontamination of the item. In the present example spaces are defined for recording the type of device to be decontaminated, its reference number, its method of decontamination, and other details including the ID number of the patient on which the device has most recently been used, the date and time of decontamination, and the name and signature of the responsible person. The record sheet permits recording of the pre-clean wipe process, the sterilising process, and the rinse wipe process. It also provides information as to the immediate destination of the decontaminated item—either for use with the patient or return to storage.

For each decontamination history of each device on the record sheet 36 there is provided a space 42 for receiving a record book label 38 from the back of the sterilising wipe sachet 20. The user peels the sticky label 38 off the sachet and affixes it in the space 42 as proof that the sterilising wipe 18 has been used, and marks adjacent boxes to confirm that the wipe 18 has been properly activated by following the specified steps. If the decontaminated device is to be returned for use on the specified patient, this information is recorded on the record sheet. Alternatively, if the device is to be returned to storage, a second sticky label, the 'patient's notes label' 46 is peeled off the sterilising wipe sachet 20 and affixed in another box 44 on the record sheet 36. This embodiment of the invention therefore provides a traceability system which uses the sterilising wipe sachet 20 as evidence that the wipe has been used as a single-use process, uniquely identified to a specific instrument at a specific time and date.

Experimental Results

Experiment 1

Sterising wipes 18 in accordance with one aspect of the invention were tested and compared with conventional wipes saturated with isopropanol (IPA), a general-purpose detergent, and sterile deionised water.

The test method to evaluate effectiveness of the wipes in killing/removing test organisms dried onto test surfaces, involved the following steps.

1. Mark out a six inch (30.5 cm) square test area on the test surface.

2. Inoculate the test surface with 0.5 ml of test organism suspension.

3. Spread the inoculum over the test area using a plastic spreader.

4. Allow the inoculum to dry (about 30 minutes).

5. Don a pair of disposable plastic gloves.

6. Prepare a $ClO_2$ wipe in accordance with the invention, using a prescribed mixing time.

7. Wipe the test area for the prescribed wiping time.

8. Place the wipe in 10 ml of universal neutraliser in a Universal bottle (Test Suspension A). Vortex stir to release organisms.

9. Wipe the entire test area with a cotton-tipped swab (thoroughly/10 times).

10. Dip the swab into 10 ml of universal neutraliser in a Universal bottle after each sampling of the test area and rotate the swab against the inner wall of the bottle to release organisms (Test Suspension B).

11. Prepare 5 serial deci-dilutions of Test Suspension A and Test Suspension B in diluent.

12. Inoculate 0.5 ml of each dilution onto a culture plate and spread using a plastic spreader. Incubate the plates and do a viable count.

13. Calculate $\log_{10}$ reductions achieved from the difference in the initial inoculum and the number of test organisms recovered after disinfection with a $ClO_2$ wipe.

Test variables were as follows.

Test Surface

A flat stainless steel instrument tray.

Test Organism

Spores of *Bacillus subtilis* var.niger NCTC 10073 freshly prepared by the method of Beeby & Whitehouse.

Inoculum

The test surface was inoculated with $1 \times 10^8$ spores.

Suspending Fluid

Sterile deionised water.

Disinfectant Concentrations 1. 200 ppm $ClO_2$ (notional)
2. 300 ppm $ClO_2$ (notional).

Mixing Times

15+30 seconds.

Wiping Times

15+30+60 seconds.

Controls 1. 1% Hospec general purpose neutral liquid detergent (Young's Detergents)/Kimcare Medical Wipes (Kimberly-Clark).

2. Sterets Alcowipe: 70% IPA (Seton Prebbles Ltd).

3. Sterile deionised water: Kimcare Medical Wipes (Kimberly-Clark).

Results are given in Table 1.

TABLE 1

| Exp. No. | Disinfectant/ Detergent | Mixing time (seconds) | Wiping time (seconds) | VC Surface | VC Wipe |
|---|---|---|---|---|---|
| 1 | 200 ppm $ClO_2$ | 15 | 15 | 177 | 143 |
| 2 | 200 ppm $ClO_2$ | 15 | 30 | 36 | 14 |
| 3 | 200 ppm $ClO_2$ | 15 | 60 | 10 | 8 |
| 4 | 200 ppm $ClO_2$ | 30 | 15 | 800 | 300 |
| 5 | 200 ppm $ClO_2$ | 30 | 30 | 240 | 27 |
| 6 | 200 ppm $ClO_2$ | 30 | 60 | 29 | 26 |
| 7 | 300 ppm $ClO_2$ | 15 | 15 | 1240 | 330 |
| 8 | 300 ppm $ClO_2$ | 15 | 30 | 530 | 250 |
| 9 | 300 ppm $ClO_2$ | 15 | 60 | 160 | 140 |
| 10 | 300 ppm $ClO_2$ | 30 | 15 | 1450 | 900 |
| 11 | 300 ppm $ClO_2$ | 30 | 30 | 30 | 70 |
| 12 | 300 ppm $ClO_2$ | 30 | 60 | 20 | 10 |
| 13 | 1% Hospec | | 60 | $7.3 \times 10^4$ | $4.3 \times 10^5$ |
| 14 | 70% IPA | | 60 | $1.9 \times 10^4$ | $3.7 \times 10^4$ |
| 15 | Deionised $H_2O$ | | 60 | $2.0 \times 10^5$ | $3.0 \times 10^5$ |

VC = Viable Count

Interpretation of Results

1. Washing/wiping with water, neutral detergent (1% Hospec), or alcohol (70% IPA) were ineffective 2. For the notional 200 ppm $ClO_2$ wipes the best results were obtained with a mixing time of 15 seconds and a wiping time of 60 seconds.

3. For the notional 300 ppm $ClO_2$ wipes the best results were obtained with a mixing time of 30 seconds and a wiping time of 60 seconds.

4. Results for 200 ppm $ClO_2$ (notional) were surprisingly better than results for 300 ppm (notional), except for mixing times of 30 seconds combined with wiping times of at least 30 seconds.

5. A wiping time of 60 seconds achieved better results than a wiping time of 30 seconds, which in turn achieved better results than a wiping time of 15 seconds.

6. Both $ClO_2$ concentrations achieved good results after a wiping time of 60 seconds. The test surface was inoculated with $1 \times 10^8$ spores. After using the $ClO_2$ wipes, surface counts were reduced to 10 and 29 (200 ppm $ClO_2$) and to 160 and 20 (300 ppm $ClO_2$).

7. A wipe containing 200 or 300 ppm may be useful, as may mixing times of 15 or 30 seconds (or, clearly, any intermediate times). However, it is preferred that wiping times longer than 15 seconds are employed.

These results were obtained using bacterial spores. It is to be expected that a vegetative bacterium such as MRSA will be much more sensitive, so that lower $ClO_2$ concentrations and/or shorter mixing or wiping times may be effective against such bacteria.

Further experiments (2-4) were carried out using 41 gsm spunlace sheets comprised of 50.5% wood pulp and 49.5% PET. The sheets' dimensions were 160 mm×180 mm×0.36 mm. In each experiment the wipes each contained 3 ml of Solution A (formulated as set forth below), made by treating a canister of 50 wipes with 150 ml of Solution A. Each wipe was activated with 1.5 ml of Solution B (formulated as set forth below) from a foam dispenser.

| Formulation: | | |
|---|---|---|
| Ingredients | Actual % w/w | Tolerance |
| Solution A (Wipe) | | |
| 1  Citric acid C.A.S. 77-92-9 | 0.50% | +/−0.60-0.40% |
| 2  Sorbic acid C.A.S. | 0.005% | +/−0.006-0.004% |

-continued

Formulation:

| | Ingredients | Actual % w/w | Tolerance |
|---|---|---|---|
| 3 | Boric acid C.A.S. 10043-35-3 | 0.005% | +/−0.006-0.004% |
| 4 | Trisodium citrate C.A.S. 68-04-02 | 0.25% | +/−0.30-0.20% |
| 5 | Trisodium phosphate C.A.S. 10101-89-0 | 0.35% | +/−0.45-0.25% |
| 6 | Glycerin C.A.S. 56-81-5 | 1.00% | +/−1.10-0.90% |
| 7 | Benzotriazole C.A.S. 95-14-7 | 0.10% | +/−0.15-0.05% |
| 8 | Sodium molybdate C.A.S. 10102-40-6 | 0.10% | +/−0.15-0.05% |
| 9 | Sodium nitrate C.A.S. 7631-99-4 | 0.20% | +/−0.25-0.15% |
| 10 | Preservative (Paramotol) C.A.S. | 0.15% | +/−0.20-0.10% |
| 11 | Deionised water C.A.S. 7732-18-5 | Balance | Balance |
| | Solution B (Foam) | | |
| 1 | Sodium chlorite (25% solution) | 0.75% | +/−0.85-0.65% |
| 2 | Cocamidopropyl betaine | 3.00% | +/−3.10-2.90% |
| 3 | Indicator/colour solution (Indicator is cosmetic yellow, No. 5, cl 19140 at 1% solution - 0.6%) | 0.60% | +/−0.07-0.50% |
| 4 | Preservative (Euxyl K 100) | 0.15% | +/−0.20-0.10% |
| 5 | Deionised Water (Purified) C.A.S. 7732-18-5 | 95.50% | +/−Balance |

Experiment 2

A study was carried out to compare the effectiveness of (a) $ClO_2$ wipes in accordance with the invention (b) a 70% IPA wipe (c) a neutral detergent wipe and (d) a water wipe in removing and/or killing (1) *B. subtilis* spores, and (2) *P. aeruginosa* cells dried onto the insertion tube of a flexible endoscope.

Wipes were prepared fresh as required by squirting foam onto a wipe and then scrunching the wipe with the fingers to mix the reagents to form $ClO_2$.

Experiment 2

Test Organisms

*B. subtilis* NCTC 10073 Spores

A suspension containing approximately $10^8$ spores/ml was prepared by the method of Beeby & Whitehouse. A 1 in 10 dilution in sterile distilled water was prepared to produce a suspension containing approximately $10^7$ spores/ml.

*P. aeruginosa* NCTC 6749

A culture containing approximately $10^8$ cells/ml was prepared by inoculating a tube of nutrient broth and incubating for 18 h at 37° C.

Insertion Tube Used in Experiment 2

The insertion tube was 1 metre long, in good condition, with clear markings. The test site used was the 10 cm section between the 30 and 40 markings.

Test Method

1. Immerse a cotton-tipped swab into a suspension of spores or vegetative cells.
2. Inoculate entire surface area of test site with the suspension. Repeat several times. Regarding *B. subtilis* spores, assume that (1) the volume of inoculum=0.1 ml, and (2) the mortality rate on drying out is zero. Hence the viable count of the inoculum=approximately $10^6$ spores. Regarding *P. aeruginosa* cells, assume that (1) the volume of inoculum=0.1 ml, and (2) the mortality rate on drying out is 1 log. Hence the viable count of the inoculum=approximately $10^6$ cells.
3. Place inoculated insertion tube across the top of an empty discard jar with the 10 cm test site resting over the centre of the jar. Allow inoculum to dry out (approximately 30 minutes).
4. Don pair of disposable plastic gloves.
5. Prepare a Wipe: $ClO_2$ (scrunch time=15 sec), IPA, Hospec or water.
6. Wipe test site for the prescribed wipe time (30 sec) as follows: Wrap wipe loosely around the insertion tube and then wipe up and down the test site repeatedly.
7. Place the wipe in 20 ml of universal neutraliser in a Universal bottle. Vortex stir to release recovered spores/cells (Test Suspension A).
8. Swab entire test site with a cotton-tipped swab. Dip swab into 10 ml of universal neutraliser in a Universal bottle and rotate swab against the inner wall of the bottle to release recovered spores/cells. Repeat 10 times then break off cotton-tip of swab and leave in the neutraliser. Vortex stir to release recovered spores/cells (Test Suspension B).
9. Prepare 5 serial deci-dilutions of Test Suspension A and Test Suspension B in diluent.
10. Inoculate 0.5 ml of each dilution onto a culture plate and spread using a plastic spreader. Incubate plates. Viable count.
11. Calculate $log_{10}$ reductions achieved from the difference in the number of spores or cells inoculated onto the test site (approximately $10^6$) and the number recovered after cleaning and/or disinfection.

Wipes Used in Experiment 2

1. $ClO_2$ Wipe (scrunch time=15 seconds).
2. 70% IPA wipe: Azowipe (Vernon Carus).
3. Hospec wipe: Kimberley Clark Medical Wipe immersed in 1% Hospec and then squeezed to remove excess solution.
4. Water wipe: Kimberley Clark Medical Wipe immersed in sterile water and then squeezed to remove excess water.

Experiment 2—Results

TABLE 2

| Test Exp | Test organism | Disinfectant/ detergent | Scrunch time (sec) | Wipe time (sec) | Viable Count (0.5 ml) Surface | Viable Count (0.5 ml) Wipe |
|---|---|---|---|---|---|---|
| 1 | B. | ClO2 | 15 | 30 | 0 | 0 |
| 2 | subtilis | $ClO_2$ (repeat) | 15 | 30 | 0 | 0 |
| 3 | | 70% IPA | | 30 | $5.0 \times 10^2$ | $2.7 \times 10^3$ |
| 4 | | 1% Hospec | | 30 | $1.5 \times 10^2$ | $2.6 \times 10^3$ |
| 5 | | Water | | 30 | $3.0 \times 10^1$ | $2.5 \times 10^3$ |
| 6 | P. | $ClO_2$ | 15 | 30 | 0 | 0 |
| 7 | aeruginosa | $ClO_2$ (repeat) | 15 | 30 | 0 | 0 |
| 8 | | 70% IPA | | 30 | 2 | 0 |
| 9 | | 1% Hospec | | 30 | $6.2 \times 10^3$ | $8.0 \times 10^4$ |
| 10 | | Water | | 30 | $2.5 \times 10^4$ | $1.5 \times 10^5$ |

TABLE 3

| Exp | Test organism | Disinfectant/ detergent | Total spores/cells recovered Surface[1] | Wipe[2] |
|---|---|---|---|---|
| 1 | B. subtilis | $ClO_2$ | 0 | 0 |
| 2 | | $ClO_2$ (repeat) | 0 | 0 |
| 3 | | 70% IPA | $1.0 \times 10^4$ | $1.0 \times 10^5$ |
| 4 | | 1% Hospec | $3.0 \times 10^3$ | $1.0 \times 10^5$ |
| 5 | | Water | $6.0 \times 10^2$ | $1.0 \times 10^5$ |
| 6 | P. aeruginosa | $ClO_2$ | 0 | 0 |
| 7 | | $ClO_2$ (repeat) | 0 | 0 |
| 8 | | 70% IPA | $4.0 \times 10^1$ | 0 |
| 9 | | 1% Hospec | $1.2 \times 10^5$ | $3.2 \times 10^6$ |
| 10 | | Water | $5.0 \times 10^5$ | $6.0 \times 10^6$ |

[1]Viable count in Table 1 × 20 (0.5 ml of 10 ml neutraliser plated out).
[2]Viable count in Table 1 × 40 (0.5 ml of 20 ml neutraliser plated out).

Experiment 2—Conclusions

1. $ClO_2$ wipes were completely effective against both *B. subtilis* spores and *P. aeruginosa* cells. No spores or cells were recovered in duplicate experiments.
2. IPA wipes exhibited good activity against *P. aeruginosa* cells but did not eliminate all of the test cells—40 viable cells were recovered from the test site on the insertion tube.
3. IPA wipes were ineffective against *B. subtilis* spores. IPA proved less effective than 1% Hospec or water which may be attributable to the coagulant properties of alcohol (fixing spores on the test site).
4. Wipes saturated with 1% Hospec were ineffective against either *B. subtilis* spores or *P. aeruginosa* cells.
5. Wipes saturated with water were ineffective against either *B. subtilis* spores or *P. aeruginosa* cells.

Experiment 3

Evaluation of the Effectiveness of $ClO_2$ Wipes in Killing/Removing Methicillin Resistant *Staphylococcus aureus* (MRSA) Dried onto a Stainless Steel Test Surface Test Method The following test method was used to evaluate the effectiveness of $ClO_2$ Wipes in killing/removing test-organisms dried onto test surfaces. The test method involves the following steps:

1. Mark out an 18 inch (457.2 mm) square on the test surface.
2. Inoculate test surface with 4.5 ml of test organism suspension.
3. Spread inoculum over 18 inch (457.2 mm) square test area using a plastic spreader.
4. Allow inoculum to dry (30-60 minutes).
5. Don pair of disposable plastic gloves.
6. Prepare a $ClO_2$ Wipe using the prescribed scrunch time (15 seconds).
7. Wipe test area for the prescribed wipe time (30 seconds).
8. Place the $ClO_2$ Wipe in 20 ml of universal neutraliser in a universal bottle. Vortex stir to release organisms. (Test Suspension A).
9. Swab entire test area with a cotton-tipped swab. Dip swab into 10 ml of universal neutraliser in a universal bottle and rotate cotton-tip against the inner wall of the bottle to release organisms. Repeat 10 times. Finally, snap off cotton-tip into the neutraliser. Vortex stir to release organisms. (Test Suspension B).
10. Prepare 5 serial deci-dilutions of Test Suspension A and Test Suspension B in diluent.
11. Inoculate 0.5 ml of each dilution onto a culture plate and spread using a plastic spreader. Incubate plates. Viable count.
12. Calculate $\log_{10}$ reductions achieved from the difference in the initial inoculum and the number of test organisms recovered after cleaning/disinfection with a ClO2 Wipe.
13. Repeat above using control wipes (70% IPA, 1% Hospec & sterile water).

Variables Selected in Experiment 3

Test Surface
A flat stainless steel laboratory bench.

Test Organism
Methicillin Resistant *Staphylococcus aureus* (MRSA): a clinical isolate from the Royal Preston Hospital.

Inoculum
The test surface was inoculated with $>10^9$ bacterial cells: 4.5 ml of an overnight culture in Nutrient Broth.

Suspending Fluid
Nutrient Broth

Scrunch Time
15 seconds

Wipe Time
30 seconds

Controls
1. 70% IPA wipe: Azowipe (Vernon Carus).
2. 1% Hospec general purpose neutral liquid detergent (Young's Detergents)/Kimcare Medical Wipe (Kimberly-Clark). The wipe was immersed in 1% Hospec and then squeezed with the fingers to remove excess fluid.
3. Sterile deionised water/Kimcare Medical Wipe (Kimberly-Clark). The wipe was immersed in water and then squeezed with the fingers to remove excess fluid.

Results

TABLE 4

| Exp | Disinfectant/ detergent | Mixing time (sec) | Wiping time (sec) | Viable Count Surface | Wipe |
|---|---|---|---|---|---|
| 1 | $ClO_2$ | 15 | 30 | 0 | 0 |
| 2 | $ClO_2$ (repeat) | 15 | 30 | 0 | 0 |
| 3 | 70% IPA | | 30 | $5.5 \times 10^4$ | 9 |
| 4 | 1% Hospec | | 30 | $5.5 \times 10^4$ | $6.0 \times 10^4$ |
| 5 | Deionised $H_2O$ | | 30 | $5.7 \times 10^4$ | $5.9 \times 10^4$ |

TABLE 5

| Exp | Disinfectant/ detergent | Mixing time (sec) | Wiping time (sec) | Total number of organisms recovered Surface[1] | Wipe[2] |
|---|---|---|---|---|---|
| 1 | $ClO_2$ | 15 | 30 | 0 | 0 |
| 2 | $ClO_2$ (repeat) | 15 | 30 | 0 | 0 |
| 3 | 70% IPA | | 30 | $1.1 \times 10^6$ | $3.6 \times 10^2$ |
| 4 | 1% Hospec | | 30 | $1.1 \times 10^6$ | $2.4 \times 10^6$ |
| 5 | Deionised $H_2O$ | | 30 | $1.1 \times 10^6$ | $2.4 \times 10^6$ |

[1]Viable Count in Table 1 × 20 (0.5 ml of 10 ml neutraliser plated out).
[2]Viable Count in Table 1 × 40 (0.5 ml of 20 ml neutraliser plated out).

Interpretation of Results

1. Wiping with a ClO$_2$ Wipe for 30 seconds was completely effective. No test organisms were recovered from either the test surface or the wipes in duplicate experiments.

2. Wiping the test surface with a 70% IPA wipe (Azowipe) for 30 seconds was ineffective. This could be due to:
    (a) an exposure time of 30 seconds was not long enough to kill the MRSA
    (b) the IPA evaporated off the test surface before the minimum exposure time required to kill the MRSA
    (c) the volume of IPA on the wipe was insufficient to deal with the >10$^9$ MRSA dried onto the 18 inch test surface
    (d) a combination of the above.

3. Only 360 test organisms were recovered from the Azowipe. This could be due to:
    (a) entrapment of test organisms in the fibres
    (b) incomplete/slow neutralisation of the residual IPA on the wipe by the neutraliser
    (c) a combination of the above 4. Wipes saturated with either 1% Hospec or sterile water were ineffective.

Experiment 4

This experiment was carried out to evaluate the effectiveness of ClO$_2$ Wipes in killing/removing spores of *Bacillus subtilis* var. niger NCTC 10073 dried out for 24 h at room temperature on a stainless steel test surface.

Test Method

1. Mark out a 12 inch (304.8 mm) square on the test surface.
2. Inoculate test surface with 1.0 ml of aqueous spore suspension.
3. Spread inoculum over 12 inch (304.8 mm) square test area using a plastic spreader.
4. Allow inoculum to dry out naturally at room temperature for 24 h.
5. Don pair of disposable plastic gloves.
6. Prepare a ClO$_2$ Wipe using the prescribed scrunch time (15 seconds).
7. Wipe test area for the prescribed wipe time (30 seconds).
8. Place the ClO$_2$ Wipe in 20 ml of universal neutraliser in a universal bottle. Vortex stir to release organisms. (Test Suspension A).
9. Swab entire test area with a cotton-tipped swab. Dip swab into 10 ml of universal neutraliser in a universal bottle and rotate cotton-tip against the inner wall of the bottle to release organisms. Repeat 10 times. Finally, snap off cotton-tip into the neutraliser. Vortex stir to release organisms. (Test Suspension B).
10. Prepare 5 serial deci-dilutions of Test Suspension A and Test Suspension B in diluent.
11. Inoculate 0.5 ml of each dilution onto a culture plate and spread using a plastic spreader.
12. Repeat above using a control wipe (a Medical Wipe saturated with sterile water).
13. Incubate plates. Viable count.
14. Calculate log$_{10}$ reductions achieved using the ClO2 Wipe from the difference in viable count obtained using the ClO2 Wipe and the control wipe.

Variables Selected in Experiment 4

Test Surface

A flat stainless steel instrument tray.

Test Organism

*Bacillus subtilis* var. niger NCTC 10073. A spore suspension was prepared by the method of Beeby & Whitehouse.

Inoculum

The test surface was inoculated with (a) 10$^6$ spores, and (b) 10$^8$ spores.

Suspending Fluid

Deionised water.

Drying Time

The inoculated instrument tray was allowed to dry out naturally at room temperature for 24 h in a dark cupboard.

Scrunch Time 15 seconds.

Wipe Time 30 seconds.

Control

1. Sterile deionised water/Kimcare Medical Wipe (Kimberly-Clark). The wipe was immersed in water and then squeezed with the fingers to remove excess fluid.

Results

TABLE 6

| Exp. | Inoculum (spores) | Disinfectant/ detergent | Mixing time (sec) | Wiping time (sec) | Viable Count Surface | Viable Count Wipe |
|---|---|---|---|---|---|---|
| 1 | 10$^6$ | ClO2 | 15 | 30 | 0 | 0 |
| 2 | 10$^6$ | Water | 15 | 30 | 2.0 × 10$^2$ | 2.1 × 10$^2$ |
| 3 | 10$^8$ | ClO2 | 15 | 30 | 4.8 × 10$^2$ | 1.3 × 10$^2$ |
| 4 | 10$^8$ | Water | 15 | 30 | 6.6 × 10$^4$ | 1.9 × 10$^5$ |

TABLE 7

| Exp. | Inoculum (spores) | Disinfectant/ detergent | Mixing time (sec) | Wipe time (sec) | Total number of spores recovered Surface[1] | Total number of spores recovered Wipe[2] |
|---|---|---|---|---|---|---|
| 1 | 10$^6$ | ClO2 | 15 | 30 | 0 | 0 |
| 2 | 10$^6$ | Water | 15 | 30 | 4.0 × 10$^3$ | 8.4 × 10$^3$ |
| 3 | 10$^8$ | ClO2 | 15 | 30 | 9.6 × 10$^3$ | 5.2 × 10$^3$ |
| 4 | 10$^8$ | Water | 15 | 30 | 1.3 × 10$^6$ | 7.6 × 10$^6$ |

[1]Viable Count in Table 1 × 20 (0.5 ml of 10 ml neutraliser plated out).
[2]Viable Count in Table 1 × 40 (0.5 ml of 20 ml neutraliser plated out).

Interpretation of Results

1. Spores dried out for 24 h at room temperature on a stainless steel test surface were not easy to dislodge using a Medical Wipe saturated with deionised water. With the 10$^6$ inoculum the recovery was 4.0-8.4×10$^3$ spores leaving 2-3 log$_{10}$ spores on the surface (assuming no mortality). With the 10$^8$ inoculum the recovery was 1.3-7.6×10$^6$ spores leaving 1-2 log$_{10}$ spores on the surface.

2. ClO$_2$ Wipes were effective in killing/removing spores dried out for 24 h at room temperature on the stainless steel test surface. With the 10$^6$ inoculum, no spores were recovered from either the surface or wipe which represents a 3-4 log$_{10}$ reduction on both the surface and wipe. With the 10$^8$ inoculum, a 2-3 log$_{10}$ reduction of spores was achieved on the surface and a 3-4 log$_{10}$ reduction on the wipe.

Thus, the invention provides a decontamination system which can be prepared in situ and which provides bactericidal, fungicidal, virucidal, and sporicidal fabrics. The system is particularly useful for sterilising wipes and for the dressing of wounds and ulcers.

To promote and accelerate the production of $ClO_2$ from the solutions we have found that acetic anhydride and ascorbic acid may advantageously be employed together as additives in Solution A. A preferred concentration for each additive is 0.4%

It is appreciated that certain features of the invention which are, for clarity, described in the context of separate embodiments, may also be provided in combination in a single embodiment. Conversely, various features of the invention which are, for brevity, described in the context of a single embodiment, may also be provided separately, or in any suitable combination. It is to be recognized that various alterations, modifications, and/or additions may be introduced into the constructions and arrangements of parts described above without departing from the spirit and scope of the present invention. As used herein, the indefinite articles 'a' and 'an' connote 'one or more' unless the context requires otherwise.

What is claimed is:

1. A decontamination system suitable for decontaminating an exterior surface of an item of medical equipment by cleaning, disinfecting, and sterilising the item to ensure that the item is made safe after use on one patient and prior to use on a second patient, the system comprising:
   (I) a plurality of pre-clean wipes comprising moist fabric members containing at least one surfactant for wiping an item to be decontaminated;
   (II) a two-part sterilant system comprising:
      (a) a first part comprising a first reagent in a carrier medium; and
      (b) a second part which is miscible with the first part and which comprises a second reagent in a carrier medium;
   wherein the first reagent and the second reagent will react when mixed to provide a chlorine dioxide containing sterilising composition;
   the first part being contained in a dispenser whereby it may be dispensed as a fluid, and the second part being absorbed or impregnated in a plurality of sterilising wipes each of which comprises a fabric member in a sealed container; and
   (III) a plurality of rinse wipes, each rinse wipe comprising an agent for neutralising an active ingredient of the sterilising composition, and a moist, sterile, fabric member in its own sealed container, wherein the decontamination system provides for decontaminating an item of medical equipment by cleaning, disinfecting, and sterilising the exterior surface of the item to ensure that the exterior surface of the item is made safe after use on one patient and prior to use on a second patient.

2. A decontamination system according to claim 1, further comprising a record sheet for recording information concerning decontamination of an item of equipment.

3. A decontamination system according to claim 2, wherein each sterilising wipe is provided in its own sealed container and each of said containers carries on an outer surface a removable adhesive label which provides information about the contents of the container including at least one of: the lot or batch number; the date of manufacture; a use-by or expiry date; and
   wherein said record sheet includes a space for receiving said label.

4. A decontamination system according to claim 3, wherein said record sheet comprises a logbook which carries pre-defined spaces for receiving adhesive labels from each container for said sterilising wipes.

5. A decontamination system according to claim 1, wherein said first part includes a foam promoter and is contained in a trigger-operated foam dispenser.

6. A decontamination system according to claim 1, wherein at least one of said first part and said second part includes an indicator reagent that changes colour when the parts are mixed together.

7. A decontamination system according to claim 6, wherein said first part and said second part have a different pH and wherein the indicator reagent changes colour in response to a change in pH when the parts are mixed.

8. A decontamination system according to claim 1, wherein one of said first part and said second part comprises a solution containing sodium chlorite or sodium chlorate and the other comprises an acidic solution.

9. A decontamination system according to claim 8, wherein the acidic solution comprises a solution of citric acid, sorbic acid and boric acid.

10. A decontamination system according to claim 1, wherein said first part further comprises from 0.1 to 50% w/w of at least one foam promoter.

11. A decontamination system according to claim 8, wherein said first part comprises said solution of sodium chlorite or sodium chlorate.

12. A decontamination system according to claim 1, wherein one of said first part and said second part further comprises from 0.1 to 50% w/w of a humectant.

13. A decontamination system according to claim 1, wherein when equal weights of said first part and the second part are mixed they provide a sterilising composition having a pH of from 4.5 to 6.5.

14. A decontamination system according to claim 1, wherein said pre-clean wipes contain at least one surfactant.

15. A decontamination system according to claim 1, wherein said pre-clean wipes contain at least one enzyme for digesting or solubilizing organic deposits.

16. A decontamination system according to claim 1, wherein said sterilant system will produce an oxidising agent when the first and second parts are mixed, and wherein said rinse wipes contain an antioxidant to at least partly neutralise or reduce said oxidising agent.

17. A decontamination system according to claim 16, wherein said oxidising agent is $ClO_2$ and said antioxidant is sodium thiosulphate.

18. A decontamination system according to claim 1, wherein said rinse wipes further contain at least one component selected from: a sequestering agent, a lubricant, and a preservative.

19. A decontamination system according to claim 1, wherein each pre-clean wipe, each sterilising wipe, and each rinse wipe is provided in its own sealed sachet.

20. A decontamination system according to claim 1, wherein the item of medical equipment comprises an endoscope.

21. A decontamination system according to claim 1, wherein the pre-clean wipes comprise enzyme for digesting or solubilizing organic deposits, humectant, buffers, preservative, corrosion inhibitor, solvent, or anti-foaming agent.

22. A decontamination system according to claim 1, wherein the rinse wipes are gamma-irradiated before being sealed in the sealed container.

23. A decontamination system according to claim 1, wherein the rinse wipes are gamma-irradiated after being sealed in the sealed container.

* * * * *